United States Patent [19]

Douvas et al.

[11] 4,200,106

[45] Apr. 29, 1980

[54] FIXED ARC CYCLIC OPHTHALMIC SURGICAL INSTRUMENT

[76] Inventors: Nicholas G. Douvas, 4200 N. Gratiot, Port Huron, Mich. 48060; Henry T. Dinkelkamp, 200 W. Orchard Pl., Mt. Prospect, Ill. 60056

[21] Appl. No.: 841,109

[22] Filed: Oct. 11, 1977

[51] Int. Cl.² .................................................. A61B 17/32
[52] U.S. Cl. ...................................................... 128/305
[58] Field of Search ............... 128/305, 276, 310, 213; 30/263, 240, 205, 208, 209; 310/36, 39, 38

[56] References Cited
U.S. PATENT DOCUMENTS

| | | | |
|---|---|---|---|
| 1,663,761 | 3/1928 | Johnson | 128/305 |
| 1,860,409 | 5/1932 | Flink | 30/240 |
| 2,387,633 | 10/1945 | Alpert | 30/240 |
| 3,486,148 | 12/1969 | Christensen | 310/36 X |
| 3,678,308 | 7/1972 | Howe | 310/36 |
| 3,783,312 | 1/1974 | Schindel et al. | 310/36 |
| 3,832,776 | 9/1974 | Sawyer | 128/305 X |

Primary Examiner—Robert W. Michell
Assistant Examiner—Michael H. Thaler

Attorney, Agent, or Firm—Harness, Dickey & Pierce

[57] ABSTRACT

A fixed arc cyclic cutter-extractor and handpiece assembly for use in ophthalmic microsurgery incorporates a tubular cutter tip having a closed outer end and a lateral orifice therethrough in close proximity to the end. The periphery of the orifice defines a cutting edge for cooperation with a cutter blade component which is of segmental cross section and is oscillatable therewithin throughout an angular path of travel which carries it between two extreme positions, in one of which positions it closes the orifice, to complete a shearing action and in the other of which the orifice is open. The cutter blade is formed as an anterior continuation of, and driven by, a combined driving and extraction tube fitted within said tubular cutter tip. An infusion tube concentrically surrounds the tubular cutter tip in the area posterior to the cutting orifice. The integral cutter blade-driving-extraction tube component is driven by a low voltage D.C. electric motor alternately energized in opposite directions and controlled in such manner as to end each cutting cycle with the blade in an open position.

3 Claims, 9 Drawing Figures

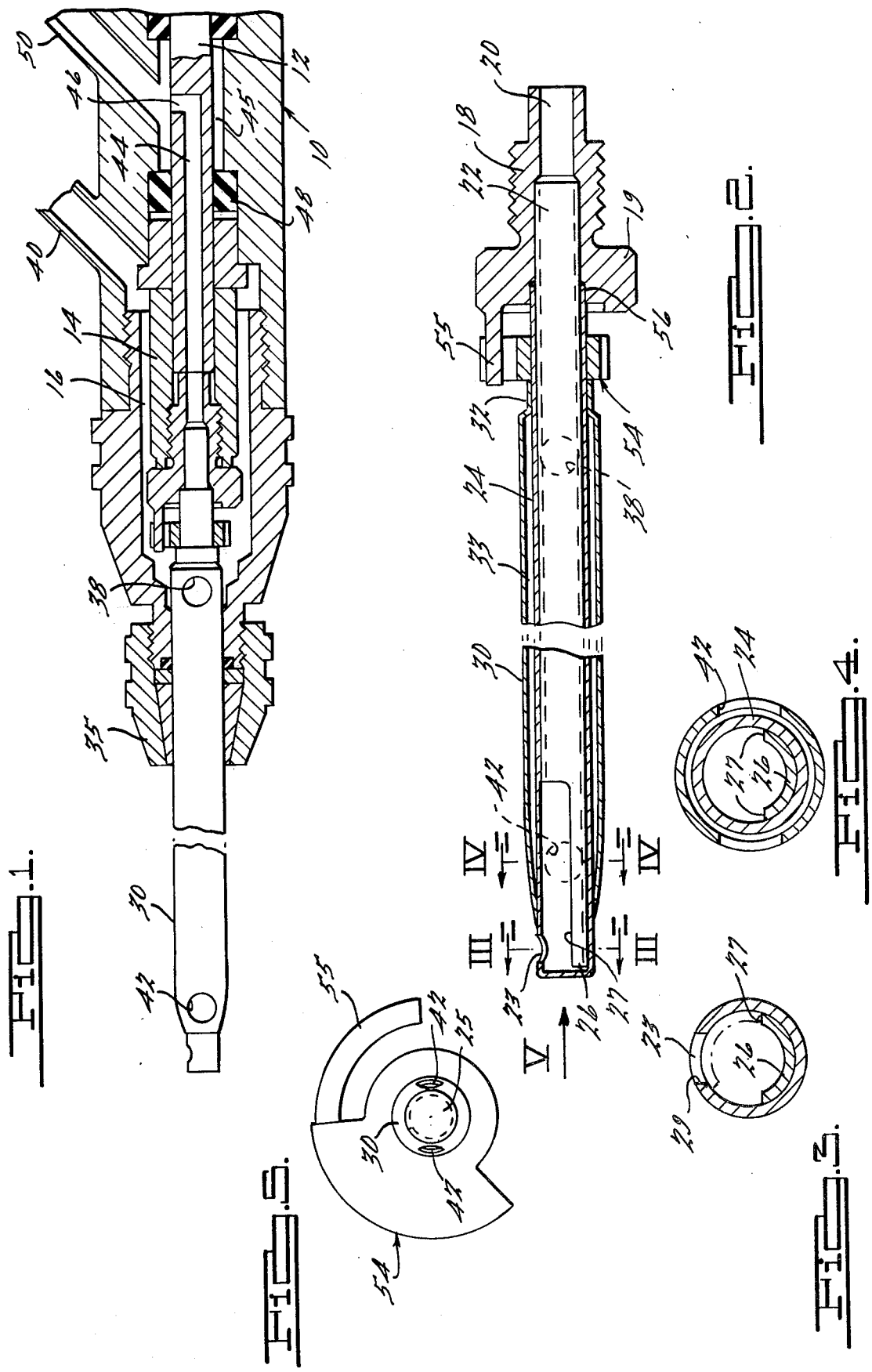

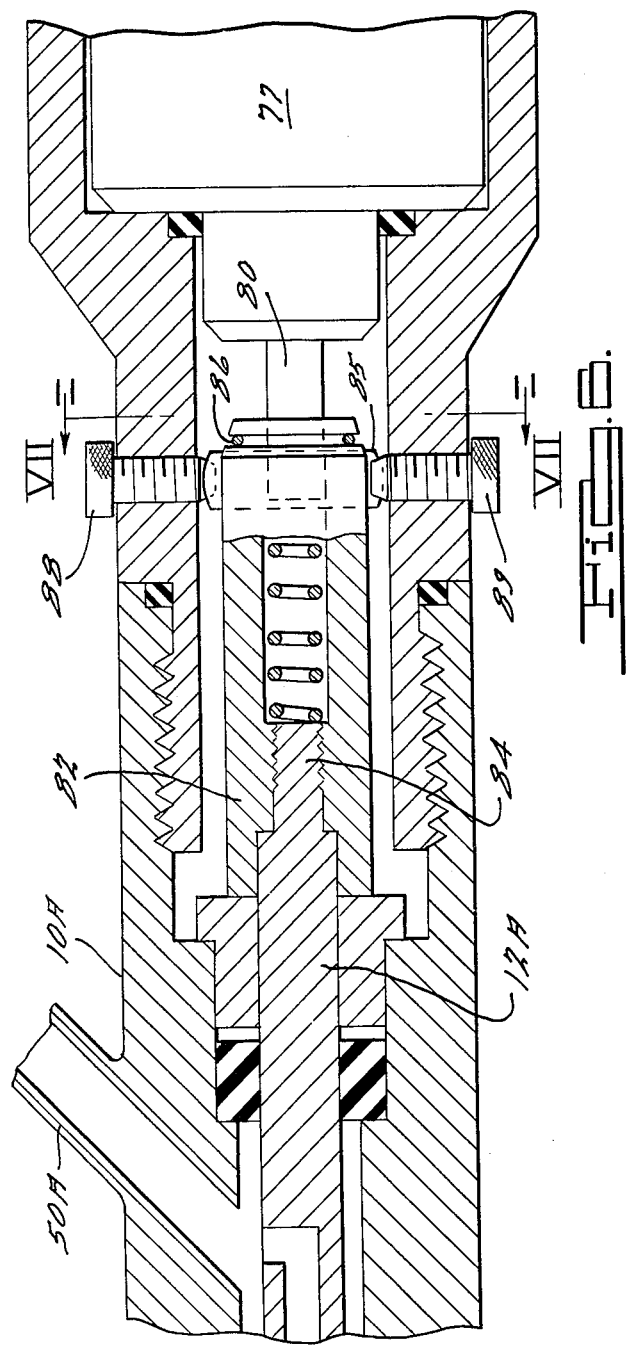

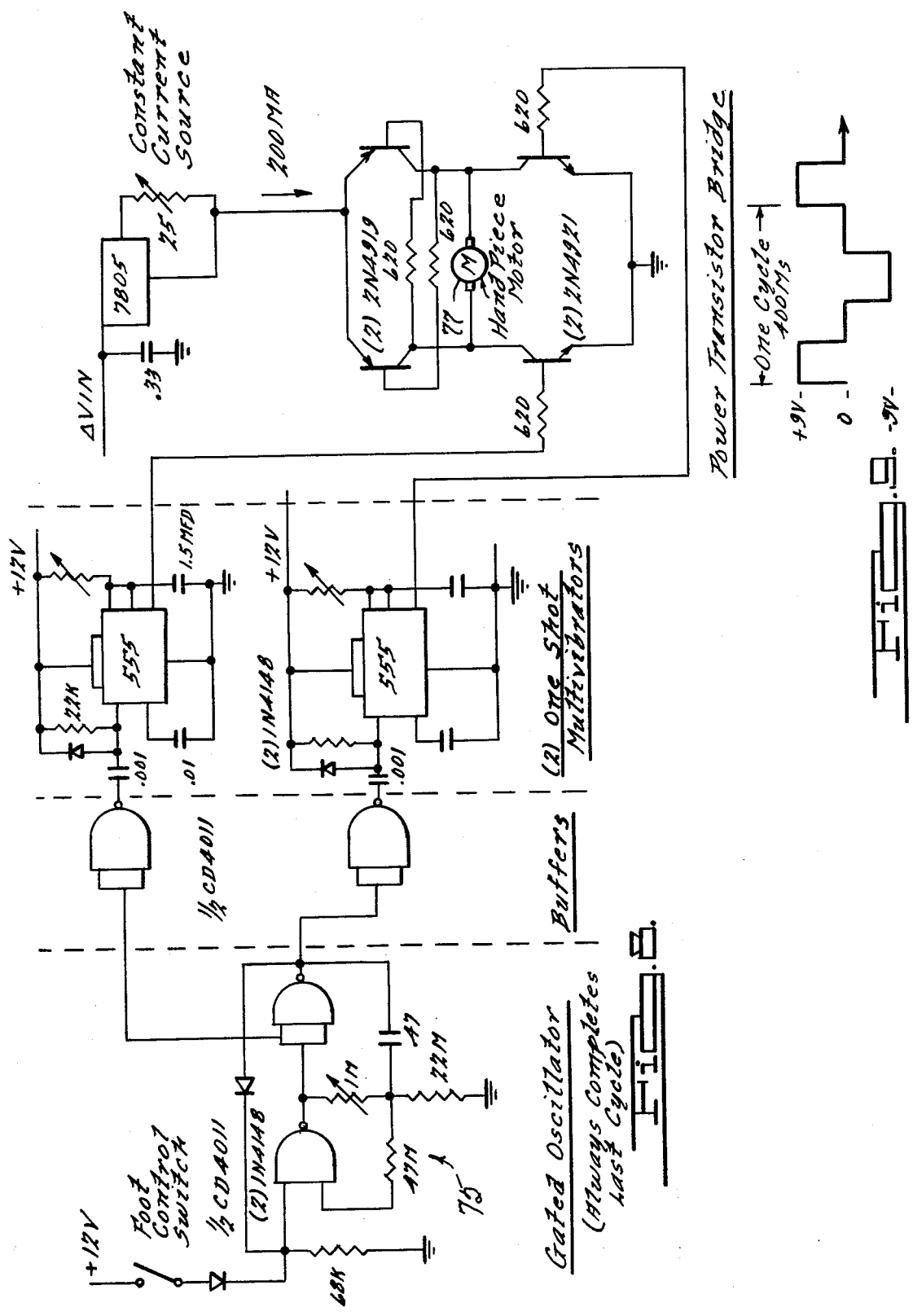

FIXED ARC CYCLIC OPHTHALMIC SURGICAL INSTRUMENT

BACKGROUND OF THE INVENTION

Many types and designs of power driven cutters for intraocular microsurgery have been developed and used. Such cutters typically incorporate means for extracting severed material, and for the infusion of fluid, and have commonly been of two basic configurations, one configuration being of the end cutting or trephining type, and the other designed for side cutting. Side cutters generally incorporate a closed-end tube having a lateral orifice near its end which functions both as a cutting edge and an infusion inlet and within which a cutter rotates or reciprocates so as to coact with the periphery of the orifice and shear material which penetrates the orifice.

In order to afford the surgeon the greatest possible working range, the cutting orifice, in rotary-type side cutters, is placed close to the distal end; to permit working as close to the retina as possible, for example. With cutters of the axially reciprocatable type it is not possible to place such opening as close to the end as is desirable, due to the room required for travel of the cutter.

Side cutters of the rotary type allow placement of the cutting orifice close to the end, and thus afford a greater range, and have been successfully employed. Great care is necessary, however, to insure that such cutters are always perfectly sharp. If used when even slightly dulled or damaged in the cutting area, there is danger that tissue will be spooled or wound on the rotating cutter.

The overall objective of the present invention is to provide an improved side-action microsurgical cutter-extractor instrument having an oscillatory cutting action.

A related object is to provide such an instrument incorporating a cutting blade portion of segmental cross section, the operating cycle of which commences and ends at a desired position, such, for example, that the orifice is fully open, and the shearing action of which is performed by angular reciprocating travel of less than one full revolution and preferably less than 120°, and in the closed position of which the leading edge of the cutter blade slightly overlaps the farther edge of the orifice.

Another object is to provide such an instrument which is convenient to use, simple and reliable, and easy to disassemble to permit sterilization and interchange of cutters.

A further object is to provide such an instrument which is capable of single cycle operation, and which is readily adjustable in such manner as to be operable either in a reciprocatory or a continuously rotatable mode.

Other objects and advantages will become apparent upon consideration of the present disclosure in its entirety.

BRIEF DESCRIPTION OF THE FIGURES OF DRAWING

FIG. 1 is a view on an enlarged scale, partly in longitudinal diametric cross section and partly in side elevation, of an instrument incorporating the principles of the present invention, partly broken away;

FIG. 2 is a longitudinal diametric section of the cutter assembly on a still larger scale, also centrally broken away;

FIGS. 3 and 4 are cross sections on a still larger scale, taken substantially on the lines III—III and IV—IV respectively of FIG. 2 and looking in the direction of the arrows;

FIG. 5 is an end elevational view taken substantially as indicated by the arrow designated V in FIG. 2;

FIG. 6 is a fragmentary enlarged view partly in diametric longitudinal section and partly in side elevation fragmentarily illustrating a handpiece incorporating abutment portions of modified construction;

FIG. 7 is a cross sectional view taken substantially on the line VII—VII of FIG. 6 and looking in the direction of the arrows;

FIG. 8 is a schematic diagram of a suitable circuit for controllingly energizing the driving motor; and FIG. 9 is a wave form diagram.

DETAILED DESCRIPTION OF PREFERRED FORMS OF THE INVENTION

Reference character 10 designates generally the forward end portions of a handpiece of a known commercially available type, the construction of which is disclosed in our prior U.S. Pat. Nos. 3,990,453, granted Nov. 9, 1976 and 3,882,872, granted May 13, 1975. The handpiece, the details which will require no specific redescription, incorporates a low voltage D.C. electric motor 77 (not shown in FIG. 1) which drives a shaft 12 suitably journaled in the body and connectable by suitable means including a coupling portion 14 to any of various types of cutter elements adapted to be detachably affixed thereto. In the construction illustrated in FIG. 1, the cutter assembly is formed of stainless steel and is connectable to the outer end of the coupling portion 14, which lies within a chamber 16 and has at its end an internally threaded socket portion adapted to threadably receive the externally threaded coupling portion 18 of the cutter assembly.

The coupling portion 18 of the cutter assembly has an axial channel 20 therethrough. A combined driving, aspirating and cutter tube 22 constitutes the inner element of a three tube cutter assembly. Inner tube 22 is fast in and projects forwardly from the coupling portion 18 and communicates interiorly with channel 20. Tube 22 is rotatably fitted in a stationary middle tube 24. Near its closed distal end 25 the tube 24 is provided with a circular radially directed cutter orifice 23. The wall of the inner tube 22 is cut away near its distal end to define a segmental cutter portion 26 which is flared both longitudinally and radially to maintain a resilient wiping engagement between the cutting edges 27 of portion 26 and the internal wall of tube 24 at the position occupied by the orifice 23.

At a position spaced slightly to the rear of the orifice 23 a concentrically outspaced outer infusion tube 30 is secured in peripherally sealed relation to the outside diameter of tube 24. Outer tube 30 extends rearwardly from such position to a position, designated 32, spaced from the rear end of tube 24, where it is necked inwardly and secured to tube 24 in sealed relation. The intermediate peripherally outspaced portion of tube 30 provides a channel 33 for infusion fluid. Tube 30 is adapted to be gripped by the collet assembly 35 which supports the installed cutter assembly with respect to the handpiece and holds the double outer tube assembly comprising the tubes 24, 30 against rotation. When so installed, the rear portion of outer tube 30 extends into the chamber 16, where it is provided with openings 38 for infusion fluid introduced into the chamber 16 via connecting nipple portion 40. The infusion fluid flows via chamber 16, orifices 38 and channel 33 to, and outwardly from, discharge openings 42 extending through the infusion tube 30 near its distal end. The axial passage 20 in the coupling portion 18 for the cutter tube 22 communicates with an axial passage 44 in shaft 12 which extends rearwardly to a position in alignment with a second chamber 45 formed in the body of the handpiece. A lateral continuation 46 of passage 44 communicates with chamber 45. Chamber 45 is isolated from chamber 16 by means of a suitable seal 48, and suitable eduction means (not shown) is adapted to be connected to chamber 45 at the fragmentarily-illustrated nipple portion 50, to provide an aspirating connection which extends via passages 46, 44, 20 and the interior of inner tube 22 to the combined suction and cutting orifice 23.

Fast upon the assembly consisting of the integrated tubes 24, 30 at a position close to but spaced from the rear extremity of tube 24 is a sector shaped abutment element 54, which, with the outer double tube structure 24, 30, is held against rotation when the cutter assembly is held in the collet 35. A coacting longitudinally extending segmental abutment 55 attached to the coupling portion 18 and rotatable with the cutter tube 22 limits the angular movement of tube 22 to approximately 180°, as will be evident upon examination of FIG. 5. Abutment 55 is carried by an annular supporting portion 19 integral with coupling portion 18. Portion 19 is counterbored to receive and rotatably overfitted upon the rear end of tube 24 as indicated at 56.

The angular extent of the cutter portion 26 is greater than the diameter of the orifice 23, and the annular dimensions of the abutment portions 54, 55, and their orientation with respect to cutter portion 26 are such as to limit the angular rotation of cutter portion 26 in one direction to an extreme open position, shown in full lines in FIG. 3, and in the other direction to a closed position which carries the leading and cutting edge 27 of the cutter blade section counterclockwise approximately 120° to the position shown in broken lines in FIG. 3, so that it slightly overlaps the farther edge portion 29 of cutting orifice 23.

As indicated above, the handpiece corresponds to the similar unit shown in our prior patents referred to above, wherein the cutter is continuously rotatable. Although any suitable circuitry may be used in order to alternately energize the low voltage D.C. electric motor in opposite directions and to insure that the last cycle is always completed, a suitable circuit for this purpose is shown in FIG. 8. Basically, the circuit comprises a special square wave oscillator which is employed to drive two one shot multivibrators. The output of the one shot multivibrators is used to switch a power transistor bridge supplying the handpiece motor. The power to the transistor bridge is regulated, adjustable, and current limited. The power supply can be of any conventional design and accordingly is not illustrated.

The oscillator circuit, generally designated 75, is of a known and relatively common type, incorporating modifications in accordance with a disclosure published in the periodical "Electronic Design" for Jan. 1977, by Mr. Larry P. Kahhan. This arrangement provides a gated oscillator which completes the last cycle each time the system is energized.

The oscillator is in the quiescent state with the foot control switch open, as shown. If the foot switch is momentarily closed for as short a time as 50 milliseconds, the oscillator will complete a full cycle and return to the rest position. Each complete output cycle of the oscillator results in a square wave output from each of the buffers. If the foot switch is held closed, the oscillator will continue to run. If the foot switch is opened at any time during a cycle, the oscillator circuit will always complete the cycle before coming to rest.

The square wave outputs from the buffers are differentiated by the 0.001 capacitors and the 22K resistor. The resultant pulse is used to trigger a 555 integrated circuit timer chip connected as a one shot having a period of approximately 100 milliseconds. The alternating outputs of the one shots are fed to the power transistor bridge. The resultant signal wave form, shown in FIG. 9, is fed to the handpiece motor 77 to alternately drive the motor in opposite directions.

The one shots serve the important function of controlling the time during which the power is applied to the motor 77, thereby limiting the stress applied to the components in the handpiece. It will be noted that the power input to the motor is also limited in this manner. In the disclosed system it will also be noted that the total time for one full cycle of the handpiece is 400 milliseconds, and that power is applied for a period of only 100 milliseconds in each direction.

The stop means for limiting the angular degree of rotation of the cutter blade might coact with shaft means within the handpiece, rather than forming a part of the cutter assembly. A preferred construction of this type is illustrated in FIGS. 6 and 7, wherein parts corresponding to those identified in connection with the first embodiment are designated by like reference numerals distinguished by the letter "A". FIG. 6 will be recognized as illustrating (upon a still larger scale) a portion of the handpiece of the known commercial type identified previously, but showing a portion located farther to the rear, that is, toward the driving motor 77, and conforming to the construction of such commercial handpiece except in the area where the motor shaft 80 is connected to the motor coupling 82. In such area, as shown in FIGS. 6 and 7, the coupling 82 is provided at its right end with squared opening for receiving the interfitted squared end of the motor shaft, and the coupling is also provided with a diametric slot extending inwardly from its right end in which a flat key 85 is fitted and retained by a snap ring 86, the key projecting radially at both of its ends from the periphery of the coupling 82. The end of shaft 80 is also provided with a slot in its end through which the key 85 extends.

A pair of diametrically opposed abutment screws 88, 89 project radially inwardly through the wall of housing 10A of the handpiece and at their inner ends extend into the path of the ends of the key 85, thereby positively limiting the degree of angular rotation of the shaft.

No specific keying means is provided to orient the cutter with respect to the abutment means 85-88-89, inasmuch as this can be done by eye. High precision of such orientation is not necessary, although keying means could be provided.

When the screws 88, 89 are backed away from their interfering position, continuous rotation of the cutter shaft becomes possible. This is of course desirable in performing certain types of operations, and it will be recognized that simple direct energization of the motor from the source of D.C. current, bypassing the control circuit, is all that is required in order to initiate continuous rotation. It will also be recognized that in the case of the first embodiment illustrated in FIGS. 1-5 inclusive, continuous rotary operation may be had in similar fashion when using cutters which do not incorporate the abutment stop elements corresponding to portions 54, 55. Typically, continuous rotation is desired in the use of trephining cutters such as are illustrated in our aforementioned U.S. Pat. No. 3,990,453.

This Detailed Description of Preferred Forms of the invention, and the accompanying drawings, have been furnished in compliance with the statutory requirement to set forth the best mode contemplated by the inventors of carrying out the invention. The prior portions consisting of the "Abstract of the Disclosure" and the "Background of the Invention" are furnished without prejudice to comply with administrative requirements of the Patent and Trademark Office.

What is claimed is:

1. In combination with an opthalmic surgical instrument incorporating a tubular stationary cutting element having a closed distal end and a laterally directed orifice therein proximate to but spaced from its distal end and defining a cutting edge, a rotatable cutting element interfitted with the stationary cutting element and co-acting with said cutting edge to shear material which penetrates the orifice, a pair of angularly spaced abutment portions fixed with respect to said stationary cutting element, third and fourth abutment portions fast with respect to the rotatable cutting element and alternately rotatable in opposite angular directions to alternately engage and to be arrested by the abutment portions of said pair, whereby the rotation of said rotatable element is limited to less than 360°, means for alternately driving said last-named element to and away from a shearing position in which the third abutment engages one of said pair of abutment portions, the means for driving the rotatable cutting element including a D.C. electric motor, power supply and controlling means for the motor, said power supply and controlling means including a square wave alternating current supply circuit for actuating the motor in opposite directions, switching means for selectively energizing said power supply and controlling means, and means for maintaining energization of the motor until completion of a full cycle if the switching means is opened prior to the normal time of completion of a full cycle from said square wave supply circuit.

2. In combination with an opthalmic surgical instrument incorporating a tubular stationary cutting element having a closed distal end and a laterally directed orifice therein proximate to but spaced from its distal end and defining a cutting edge, a rotatable cutting element interfitted with the stationary cutting element and co-acting with said cutting edge to shear material which penetrates the orifice, a pair of angularly spaced abutment portions fixed with respect to said stationary cutting element, third and fourth abutment portions fast with respect to the rotatable cutting element and alternately rotatable in opposite angular directions to alternately engage and to be arrested by the abutment portions of said pair, whereby the rotation of said rotatable element is limited to less than 360°, means for alternately driving said last-named element to and away from a shearing position in which the third abutment engages one of said pair of abutment portions, the means for driving the rotatable cutting element including a D.C. electric motor, power supply and controlling means for the motor, said power supply and controlling means including a square wave alternating current supply circuit for actuating the motor in opposite directions and having a pulse duration shorter than the time required for said abutments to move from one extreme relative position to the other.

3. A combination as defined in claim 2 wherein said circuit also includes means for completing a full cycle if the circuit is opened during a cycle.

* * * * *